United States Patent
Peyman

(10) Patent No.: US 7,220,224 B1
(45) Date of Patent: May 22, 2007

(54) RETINAL TRANSLOCATION AND FIXATION USING ADHESIVE MATERIAL

(75) Inventor: Gholam A. Peyman, New Orleans, LA (US)

(73) Assignee: Minu, LLC, Pittsboro, NC (US)

( * ) Notice: Subject to any disclaimer, the term of this patent is extended or adjusted under 35 U.S.C. 154(b) by 600 days.

(21) Appl. No.: 10/625,543

(22) Filed: Jul. 24, 2003

Related U.S. Application Data

(60) Provisional application No. 60/452,554, filed on Mar. 7, 2003.

(51) Int. Cl.
  *A61N 5/00* (2006.01)
  *A61N 36/00* (2006.01)
  *A61B 17/08* (2006.01)
  *A61F 11/00* (2006.01)

(52) U.S. Cl. .................... 600/3; 600/8; 606/5; 606/10; 606/13; 606/108; 606/157

(58) Field of Classification Search ................. 600/3, 600/8; 606/157, 5, 108, 10, 13
  See application file for complete search history.

(56) References Cited

U.S. PATENT DOCUMENTS

| | | | |
|---|---|---|---|
| 6,217,594 B1* | 4/2001 | Hallen et al. ............... | 606/157 |
| 6,509,355 B1* | 1/2003 | Collier et al. ............... | 514/317 |
| 6,875,165 B2* | 4/2005 | Dejuan et al. .................. | 600/3 |
| 6,989,008 B2* | 1/2006 | Peyman .......................... | 606/5 |
| 2002/0138070 A1* | 9/2002 | Peyman .......................... | 606/5 |

OTHER PUBLICATIONS

Hayashi et al., Retinal Changes after retinal translocation surgery . . . , Investigative ophthalmology and visual science, 2000, vol. 41, pp. 4288-4292.*

* cited by examiner

*Primary Examiner*—Vickie Kim
(74) *Attorney, Agent, or Firm*—Bell, Boyd & Lloyd LLP

(57) ABSTRACT

The present invention relates to a method of displacing an area of the macula of an eye, including the steps of placing a substance below the surface of the retina, folding the retina to form a folded portion of the retina, and affixing the folded portion, so that the folded portion substantially maintains a folded shape.

7 Claims, 6 Drawing Sheets

RETINAL TRANSLOCATION AND FIXATION USING ADHESIVE MATERIAL

This application claims the benefit under 35 U.S.C. § 119(e) of provisional patent application Ser. No. 60/452,554, filed Mar. 7, 2003, the entire content of which is incorporated herein by reference.

FIELD OF THE INVENTION

The present invention relates to using retinal translocation to correct vision caused by age related macular degeneration (ARMD). More specifically, the present invention relates to detaching the retina, folding the retina and securing the folded portion, so that the fovea is moved, and thereby correcting the vision in an eye.

BACKGROUND OF THE INVENTION

Age-related macular degeneration (ARMD) is the leading cause of blindness among persons over fifty in the United States and other countries. Two forms of age-related macular degeneration are known: (1) neovascular, also known as exudative, age-related macular degeneration (E-ARMD) and (2) nonneovascular, also known as nonexudative, age-related macular degeneration (NE-ARMD). NE-ARMD is characterized by the presence of drusen, yellow-white lesions of the retinal pigment epithelium within the macula, and by other abnormalities of the retinal pigment epithelium, including retinal cell death.

Although the exact etiology of ARMD is not known, several risk factors seem to be important for the manifestation of this disease. For example, ARMD may be caused by chronic exposure of the retina to light. The presence or absence of certain nutrients in the diet, such as the antioxidant vitamins E and C, also may affect one's predisposition for ARMD. Other conditions, such as hypertension and smoking, are also considered to be important risk factors for the development of this disease.

Several therapeutic methods have been tried. For example, vitamins and dietary supplements have been used for the purpose of delaying the onset of disease. Thalidomide is being investigated to determine if it will slow down or arrest new vessel formation. Laser or radiation has been used to destroy new vessels. However, none of these methods has led to successful results and no definitive treatment for ARMD has been developed to date.

Additionally, retinal translocation has been used to change the position of the fovea. Retinal translocation is a surgical method that involves injecting a fluid, such as saline solution, under the retina to loosen the retina. Gas is then injected into the vitreous to reattach the retina, and a scleral indentation is formed. This procedure results in displacement of the retina inferiority, placing the fovea on normal retinal epithelium.

However, the retinal displacement is generally unpredictable and minimal. For example, the displacement is generally only about 500–1000 microns. Thus, there is little area for subsequent coagulation of the subretinal membrane. Additionally, the displacement does not occur immediately during surgery, but during a recovery process that generally lasts about 24 hours. The displacement occurs due to the position of the head of the patient in a recovery situation. For example, since the head is generally held in an upright manner, the gas injected into the eye rises, thus forcing the retina from the top, moving the retina inferiority with respect to its original position. Furthermore, the retina can generally only be easily moved inferiority since the gas rises up relative to the eye and can only exert pressure to move the retina down.

Additional retinal translocation procedures exist wherein the retina is literally cut 360° and disassembled for translocation relative to the underlying tissue prior to re-assembly of the retina after its rotation. This procedure has 15–30% rate of severe complication and loss of vision.

These procedures are intended to treat conditions wherein the tissue underlying the macular (central vision) portion of the retina becomes diseased. Degenerative conditions of this sort may result in the photoreceptors of the macula portion of the retina adjacent to the underlying diseased tissue becoming non-functional over time. To avoid this result, the above procedures shift the position of the fovea (i.e., the central portion of the macular portion of the retina which is responsible for a person's sharpest vision) relative to the underlying inner surface of the sclera. This allows the fovea then to be reattached to healthier underlying tissue.

To accomplish this result, the Macular Translocation Procedure, which is less radical than the Retinal Translocation procedure, includes the following steps. First, sutures are placed in a horizontal mattress formation in an arc supero-temporally (i.e., just below the attachment of the recti muscle to the sclera) on the outer surface of the sclera. These sutures typically are located in the same position relative to the eye regardless of the exact location of the diseased tissue. Then, at least the macula portion of the retina is intentionally detached from the underlying tissue. This usually is accomplished by performing a 3 port pars plana vitrectomy followed by the use of a subretinal infusion cannula and a balanced salt solution to create the desired retinal detachment. The pre-placed sutures are then tightened and tied off. This results in the creation of an inwardly extending fold in the sclera that effectively "shortens" the scleral diameter. Thereafter, an air bubble is formed inside the eye so that the excess length of the retina relative to the shortened underlying scleral surface is moved. Then, a partial air-fluid exchange is made. The natural fluid removal generated by the pigment epithelium and choroid allow the macula portion of the retina, which has been shifted relative to the underlying tissue by the deformation of the sclera and by the formation of the air bubble, to settle gradually against, and reattach itself to, healthy tissue. Finally, several days after the surgical procedure, the diseased lesion is treated with standard laser photocoagulation.

The placement of the sutures in the macular translocation procedure is time consuming and, therefore, inefficient. It is also difficult to consistently predict when the retina will settle eventually. In some cases, it may not move at all. It is also difficult to predict the distance of scleral shortening that will result upon the tightening and tie off of the sutures. Further, the skill level required to place and to manipulate the sutures without causing extraneous damage to the eye, or surrounding bodily structures, is high.

Therefore, a need exists to improve the vision in an eye that is suffering from age related macular degeneration and make the surgical results predictable and visible immediately during surgery. There is also a need to move the retina superiorly or inferiorly as desired during the surgery.

SUMMARY OF THE INVENTION

An object of the present invention is to improve the vision in an eye suffering from age related macular degeneration and other macular diseases.

A further object of the present invention is to provide a method of moving the retina to a predetermined or predictable location in the eye.

Still a further object of the present invention is to provide a method of moving the retina during the surgical procedure or shortly thereafter.

These objects are basically attained by a method of displacing an area of the macula of an eye, including the steps of placing a substance below the surface of the retina, folding the retina to form a folded portion of the retina, and affixing the folded portion, so that the folded portion substantially maintains a folded shape.

These objects are further attained by a method of forming a fold in an area of the macula of the eye, comprising the steps of forming at least one opening through an external surface of the eye, which allows access to an area of the macula by detaching the retina by injecting a physiologic solution under the retina, inserting a member through the least one opening, contacting the area of the macula with an end of the member, folding the retina to form a folded portion, injecting an adhesive under the fold, at least a portion of the solution being contained with a portion of the folded portion.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

Figure 1:
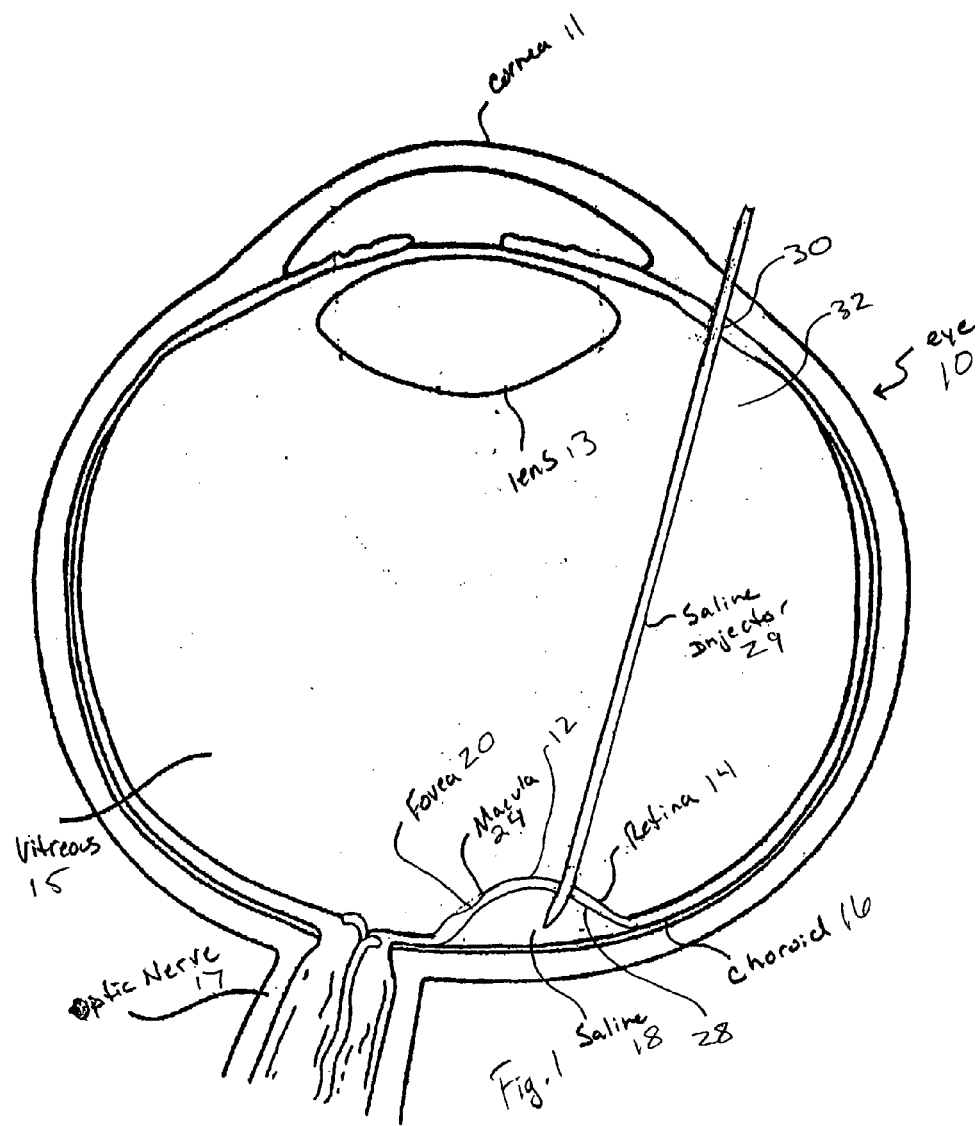
FIG. 1 an elevational side view in section, illustrating a preferred embodiment of the present invention, wherein a saline solution is being injected under the retina of an eye.

The eye 10 generally consists of a cornea 11, a lens 13, vitreous 15, the optic nerve 17 and a retina 14. As illustrated in FIGS. 1–5, the present invention relates to using retinal translocation to correct vision in eye 10 caused by age related macular degeneration. This is achieved by separating a portion 12 of the retina 14 from the choroid 16 using a substance 18 and folding the separated retinal portion 12 to move the fovea 20. The folded retinal portion 22 is then affixed to itself, preferably using a bioadhesive 26 and folding the macula on itself. The substance 18 located between the retina 14 and the choroid 16 can then be removed by using any method desired, such as air-fluid exchange surgery.

Initially, during this procedure, as shown in FIG. 1, the retina 14 is detached by inserting or injecting a substance 18 under the surface 28 of the retina 14 to form a separated retinal portion 12 using a injector 29. The substance 18 preferably is a saline solution and is inserted using a saline injector, as shown in FIG. 1, but can be any desired substance, such as any suitable gas, any suitable oil, or any suitable solid.

Each suitable substance can be inserted in any manner desired and is preferably injected, except a solid substance. When inserting a solid substance, it is preferable to form an incision in the retina and position the solid in the desired position using a grasping or gripping device, similar to device 34, described below. The incision in the retina can then be closed, if desired, using any known or conventional method.

Figure 2:
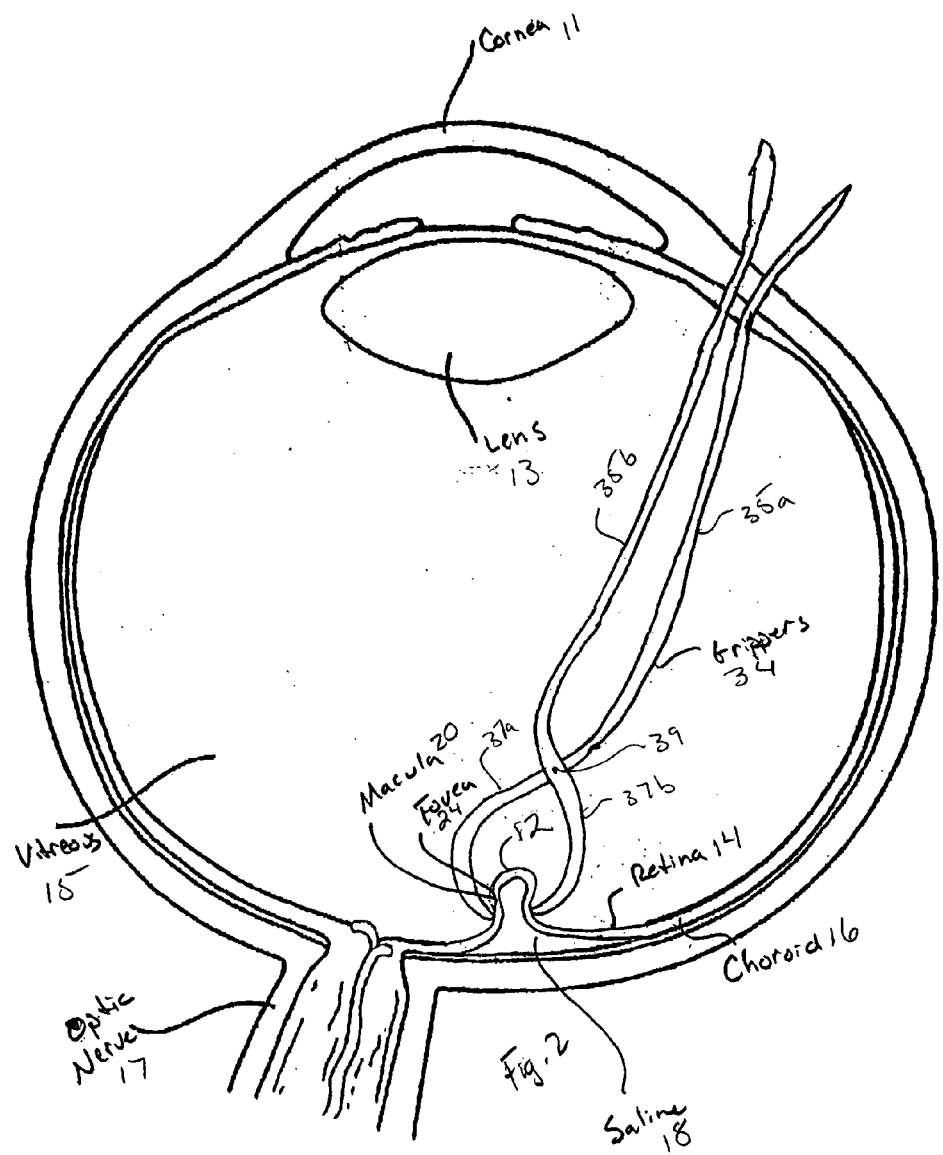
FIG. 2 is an elevational side view in section of the eye of FIG. 1 with a gripping device grasping a portion of the retina to form a folded portion.

An opening 30 is formed in the outer surface of the eye, which allows access through the eye and into the internal posterior chamber 32. As shown in FIG. 2, the separated retinal portion 12 is grasped using any suitable or desired device or member, such as a clipping or gripping device 34, which is inserted through opening 30 formed in the eye. Using device 34, the retina is then gripped or pinched and folded in the desired area. For example, the retina can be folded in the superior or the inferior area of the retina, depending on the desired direction of retinal displacement. A fold in the superior area moves the fovea upward (FIG. 6), and an inferior fold moves the fovea downward (FIG. 7), relative to the rest of the interior of the eye.

It is noted that gripping device 34 generally has a two handle portions 35a and 35b that interact with the two gripping portions 37a and 37b to squeeze or pinch the retina therebetween. Portions 35a and 35b are coupled together at junction 39, in a conventional manner. However, it is not necessary that the gripping device be constructed in this manner, and can be any type of device that would allow a fold in the retina to be formed. For example, the gripping mechanism can be two separate members that are manipulated to form the fold.

Figure 3:
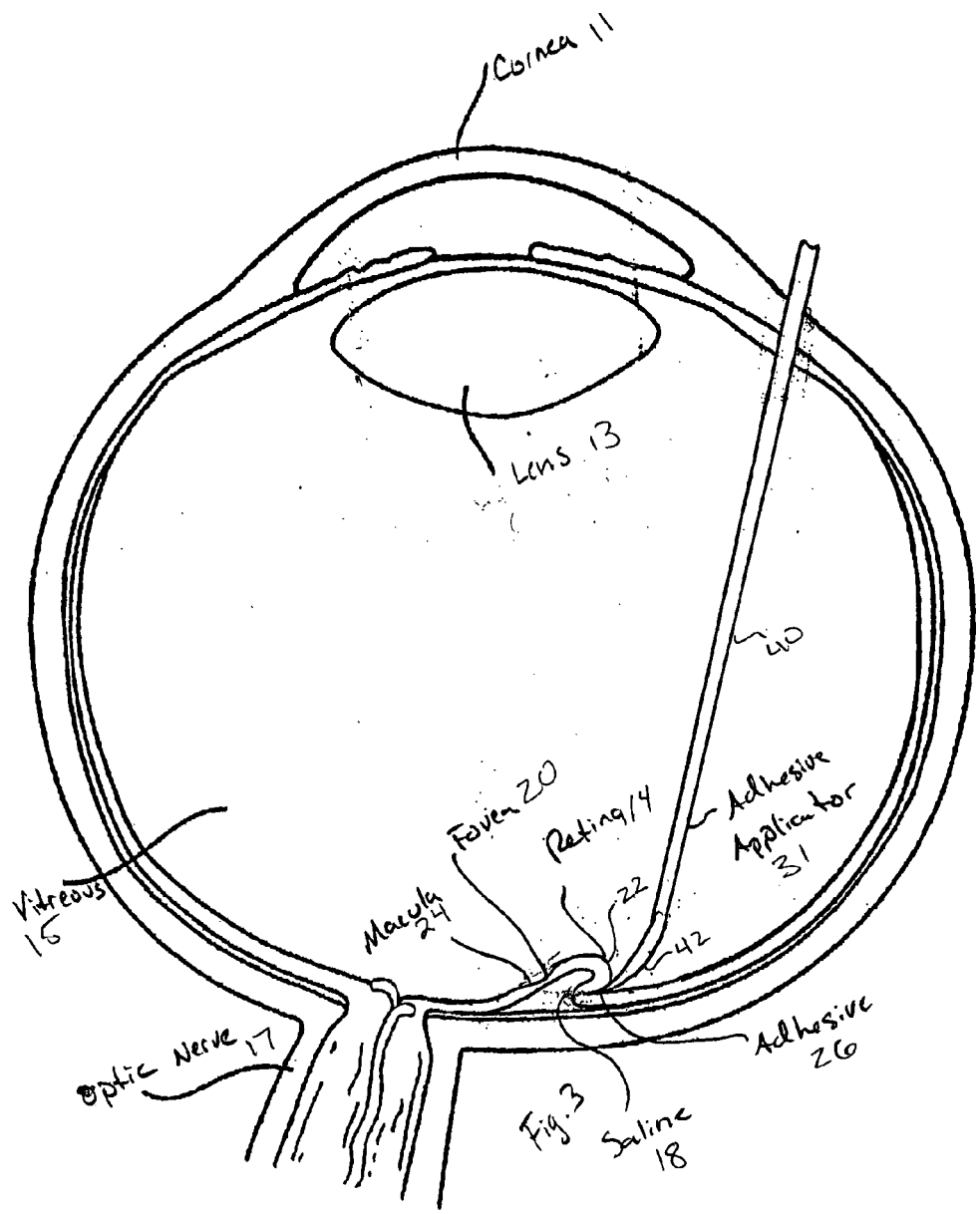
FIG. 3 is an elevational side view in section of the eye of FIG. 2 with an adhesive being applied to the folded portion to attach the folded portion to each other or to another portion of the retina.

As seen in FIG. 3, once the desired fold is formed, adhesive 26 is preferably injected under the retinal fold or inside the fold using an adhesive applicator 31, and the gripping device or member is removed through the opening 30. The adhesive can be applied to the surface of the fold or under the surface of fold to any area desired that affixes the fold to itself or to the surface of the retina. The adhesive is preferably a bioadhesive, such as polydendrimer, but it can be any suitable material. The adhesive applicator is preferably has a tube 40 that is hollow with a end portion 42 that allows the adhesive 26 to be applied therethrough.

The applicator 31 is generally connected to a reservoir (not shown) that can pump the adhesive through the applicator. However, if desired, the applicator can have a plunger or syringe type device connected thereto, which would allow application of the adhesive.

Furthermore, the adhesive can be a material that can immediately affix the fold to the retina, or a bioadhesive that can be used to activate the adhesive in response to exposure to blue light or an argon laser, which initiates polymerization of the material.

It is noted that the adhesive does not necessarily need to be applied after the fold is created and can be applied at any suitable time. For example, in any process described herein, and particularly when using an adhesive that is activated in response to a laser, the adhesive can be applied at anytime prior to, during or after the formation of the fold.

Furthermore, if desired, the fold can be affixed using any other method or device desired. For example, a clip can be used to affix the fold to the superior or inferior area of the retina, or any combination thereof. Each of these types of mechanical securement methods can be permanent, semi-permanent or temporary. For example, a biodegradable mechanical securement device can be used along with adhesive that is activated post-operatively. The mechanical device would hold the fold in place until the adhesive was activated and then biodegrade over a certain period of time.

Figure 4:
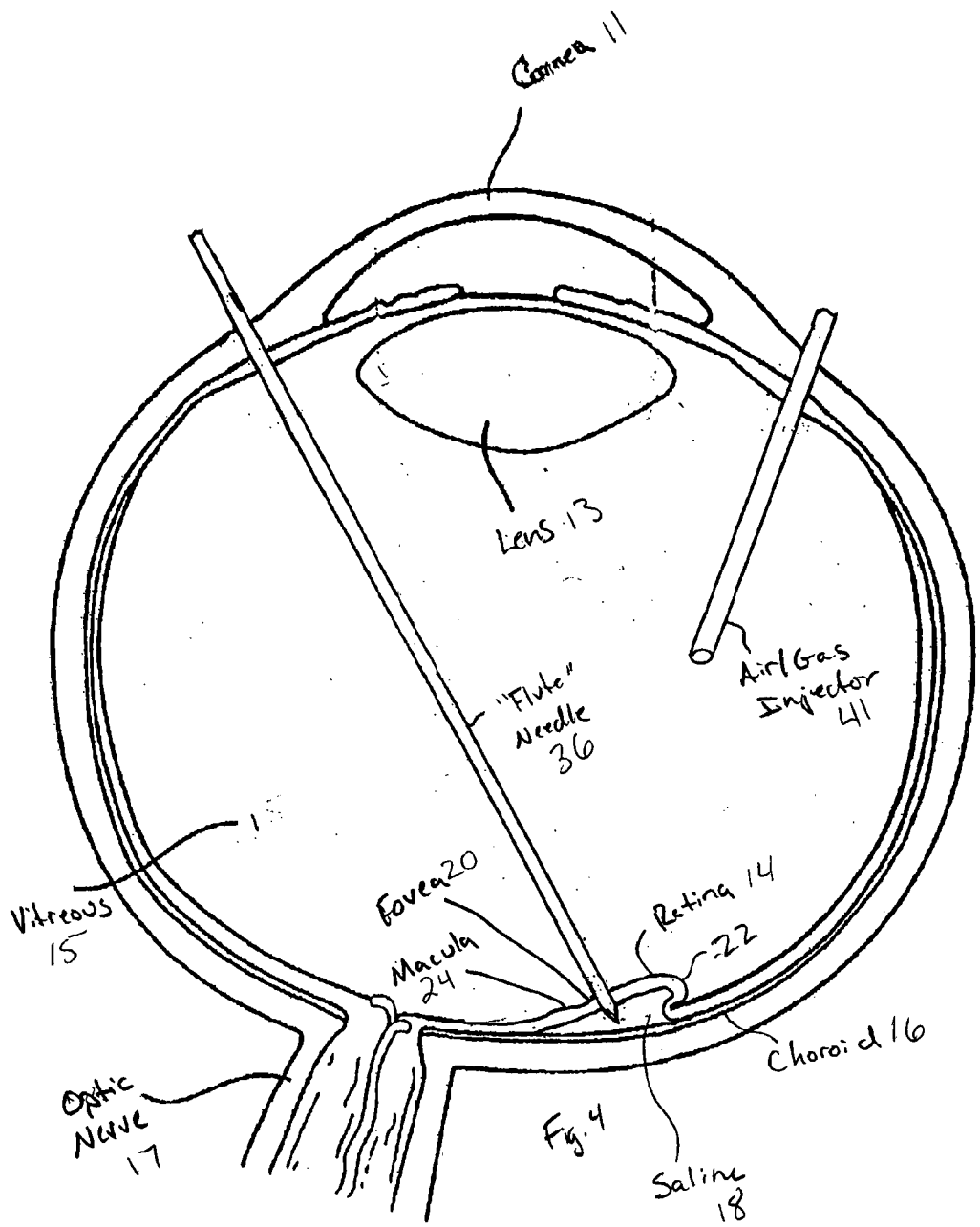
FIG. 4 is an elevational side view in section of the eye of FIG. 3 with the saline solution being removed from under the retina using standard air-fluid exchange surgery.

Once the fold is fixed in the desired position, the subretinal fluid or solution 18 is removed or withdrawn using standard air-fluid exchange surgery, wherein air is injected into the vitreous cavity using an air/gas injector 41, and the subretinal fluid is removed using a "flute" needle 36, as shown in FIG. 4.

Generally, as air or gas is pumped through the injector 41 and into the posterior chamber 32 of the eye, pressure is exerted on the folded portion 22. This pressure forced the substance 18 through the flute needle 36, and out of the eye.

Figure 5:
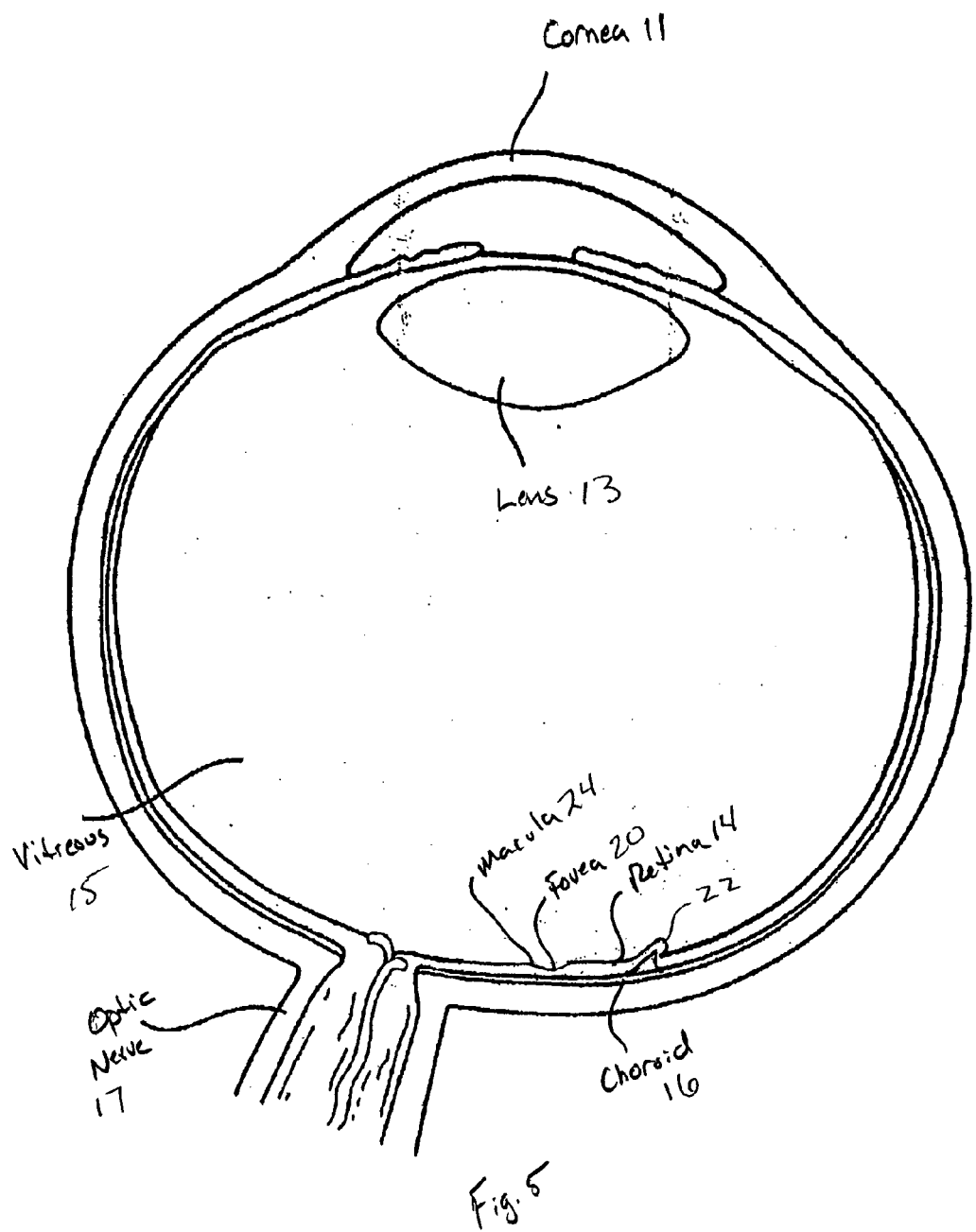
FIG. 5 is an elevational side view in section of the eye of FIG. 4 after the saline solution has been removed.

This removal of the subretinal or saline fluid results in the fovea and/or the macula being moved to a predetermined position and a predetermined distance, as shown in FIG. 5.

When using a solid to reposition the fovea, it is noted that it is not necessary to close the incision made therein, since as with the saline fluid the solid substance is removed after the fold is created. Therefore, it is preferable to have the incision left open for the purpose of removal of the substance. However, the incision can be closed and reopened for removal of the solid substance, if desired.

Furthermore, it is not necessary to close the incision after the solid substance is removed, since the incision will heal on its own. However, if desired, the incision can be closed using an suitable methods, such as bioadhesive or any other desired methods.

The choroidal or the subretinal neovascularization can be coagulated surgically or using a laser, and can be performed either intraoperatively or postoperatively, or at any time or in any suitable manner.

Figure 6:
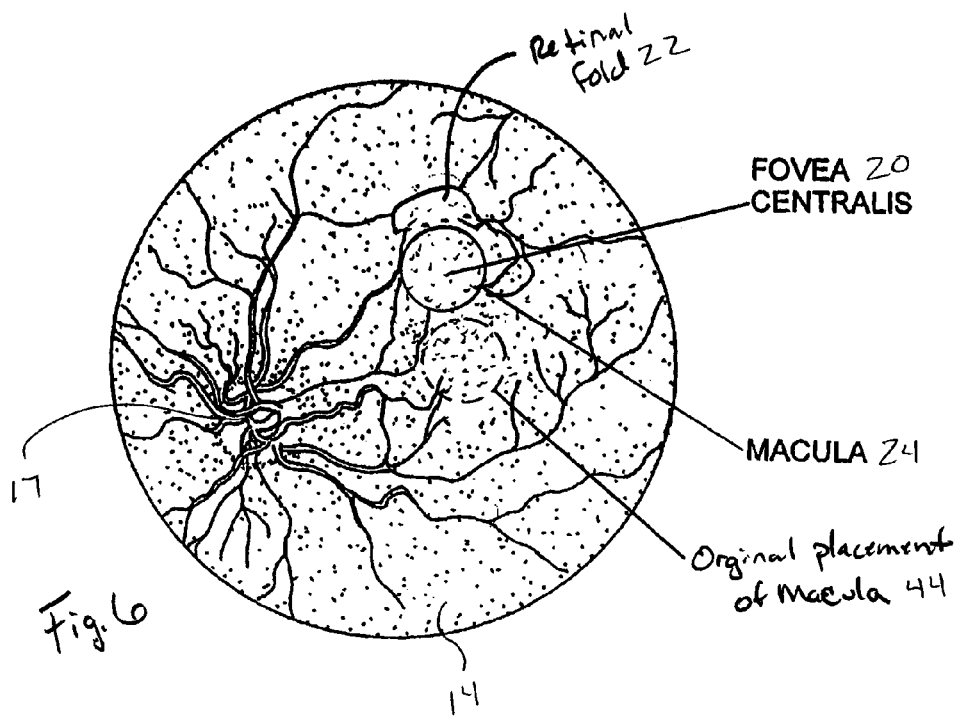
FIG. 6 is a top planar view of the retina of an eye, wherein the fovea has been moved superiority.
Figure 7:
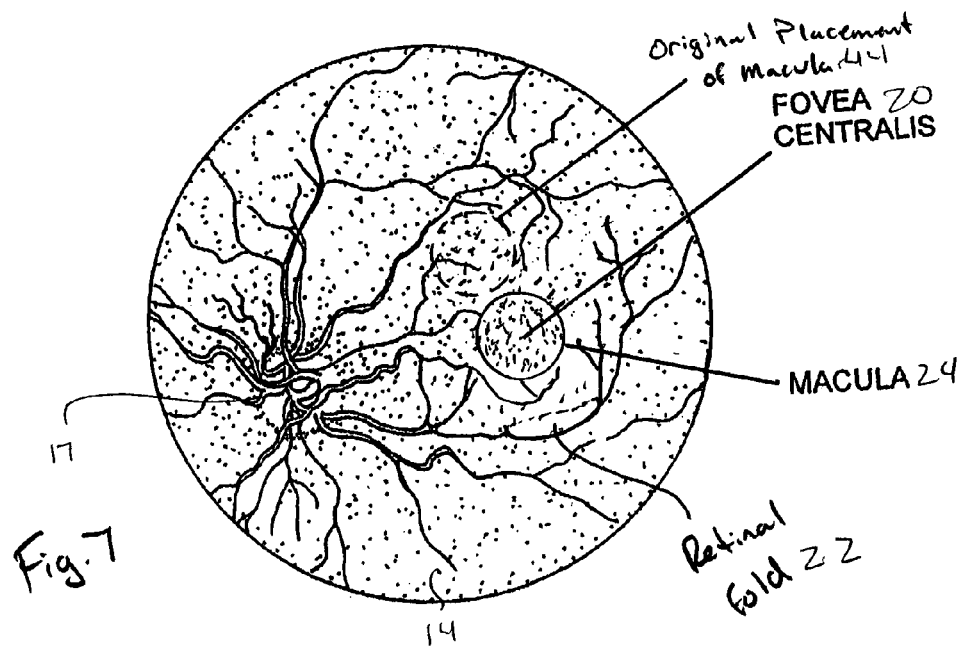
FIG. 7 is a top planar view of the retina of an eye, wherein the fovea has been moved inferiority.

As shown in FIGS. 6 and 7, the macula 24 has moved from its original position or placement 44 to a superior position (FIG. 6) or a inferior position (FIG. 7), depending on the location of the retinal fold 22.

It is noted that the fold does not necessarily need to be formed only in the inferior (FIG. 7) or superior (FIG. 6) areas. The fold can be formed in any portion of the retina that would allow the macula or the fovea to move in any direction desired. For example, a fold can be formed that would move the fovea up, down, left or right or any combination thereof, relative to the rest of the interior of the eye.

Relative directions, such as up, down, left, right, superiority and inferiority are not meant to limit the invention and are merely used to further describe and explain the present invention.

While preferred embodiments have been chosen to illustrate the invention, it will be understood by those skilled in the art that various changes and modifications can be made therein without departing from the scope of the invention as defined in the appended claims.

What is claimed is:

1. A method of forming a fold in an area of the macula of the eye, comprising the steps of
    forming at least one opening through an external surface of the eye, which allows access to an area of the macula,
    separating a portion of the macula from the choroid,
    inserting a member through the least one opening;
    contacting the area of the macula with an end of the member,
    folding the macula to form a folded portion, thereby changing the position of the fovea; and
    affixing the folded portion with a bioadhesive to retain a folded configuration, wherein said bioadhesive is polydendrimer.

2. A method according to claim 1, further comprising the steps of removing the member from the eye through the opening.

3. A method according to claim 1, wherein
    said affixing step includes suturing the folded portion so that the folded portion maintains a folded shape.

4. A method according to claim 1, further comprising the step of inserting a substance under the surface of the retina.

5. A method according to claim 4, wherein said substance is saline.

6. A method according to claim 4, wherein
    at least a portion of the substance is contained with a portion of the folded portion.

7. A method according to claim 4, further comprising
    removing the substance from below the surface of the macula.

* * * * *